United States Patent [19]

Schacher

[11] Patent Number: 5,496,519

[45] Date of Patent: * Mar. 5, 1996

[54] DIAGNOSTIC PROCESSING STATION

[75] Inventor: Gottlieb Schacher, Ebikon, Switzerland

[73] Assignee: Hoffmann-La Roche Inc., Nutley, N.J.

[*] Notice: The portion of the term of this patent subsequent to Jan. 24, 2012, has been disclaimed.

[21] Appl. No.: 278,362

[22] Filed: Jul. 21, 1994

Related U.S. Application Data

[62] Division of Ser. No. 49,753, Apr. 19, 1993, Pat. No. 5,384,094.

[30] Foreign Application Priority Data

Apr. 30, 1992 [CH] Switzerland .................... 1390/92

[51] Int. Cl.[6] ............................................. G01N 37/00
[52] U.S. Cl. ........................... 422/64; 422/63; 422/65; 422/103; 422/104; 436/43; 436/47; 436/48
[58] Field of Search ............................. 422/63, 64, 65, 422/103, 104; 436/43, 47, 48

[56] References Cited

U.S. PATENT DOCUMENTS

| | | | |
|---|---|---|---|
| 3,322,958 | 5/1967 | Heiss | 422/63 |
| 3,904,372 | 9/1975 | Lightner | 422/63 |
| 4,447,395 | 5/1984 | Englar et al. | 422/68 |
| 4,595,562 | 6/1986 | Liston et al. | 422/65 |
| 4,699,766 | 10/1987 | Yamashita | 422/64 |
| 4,755,055 | 7/1988 | Johnson et al. | 356/440 |
| 4,844,868 | 7/1989 | Rokugawa | 422/64 |

FOREIGN PATENT DOCUMENTS

92/05448  4/1992  WIPO.

OTHER PUBLICATIONS

Holen, James T., et al. IEEE Engineering in Medicine and Biology, vol. 4, No. 1, pp. 14–17 (Mar., 1985).

*Primary Examiner*—James C. Housel
*Assistant Examiner*—Long V. Le
*Attorney, Agent, or Firm*—George M. Gould; George W. Johnston; John P. Parise

[57] ABSTRACT

A processing station for making a fluorescence polarization measurement on a sample in a cell under examination in a device for chemical and biochemical analysis, the analytical device containing a conveyor for conveying cells. In order to make fluorescence polarization measurements outside the conveyor, the processing station is separated from the conveyor and contains a measuring device means for making fluorescence polarization measurements on a sample in a cell, and an automatically controlled change-over and positioning device for removing individual cells from the conveyor, transferring a removed cell to a measuring position in the measuring device, and returning the cell to its original position on the conveyor after the measurement.

2 Claims, 9 Drawing Sheets

DIAGNOSTIC PROCESSING STATION

This is a division of application Ser. No. 08/049,753, filed Apr. 19, 1993 now U.S. Pat. No. 5,384,094.

BACKGROUND

1. Field of the Invention

The invention relates to a processing station for use in conducting a fluorescence polarization measurement on a sample in a cell under examination in a device for chemical and biochemical analysis.

2. Description

Automatic analytical devices usually operate on the following principle. Samples for analysis or parts of samples are placed in containers and then subjected to a series of processing steps such as adding (pipetting) reagents, mixing or incubation. Measurements of the reactions which have taken place are made a number of times during processing and/or once at the end of processing. The usual procedure is as follows. The containers holding the samples for analysis are placed in a fixed sequence on a conveyor and travel through various processing stations. In the case of batch processing, as is usual in the case of centrifugal analytical devices, all sample containers are placed on a carrier (rotor) and subjected practically simultaneously to the processing steps and measurements. Analytical systems operating on these principles provide good service in large clinics and analytical centers where many samples have to be processed.

In view, however, of the variety of possible analyses today and the medical requirements on clinical chemistry, particularly in immunological investigations, the conventional automatic analyzers for throughput of large quantities of samples are not sufficiently flexible to provide analytical profiles (full random access) specifically adapted to individual patients or clinical pictures. It is an aim of this invention to achieve increased flexibility. In addition to photometric extinction measurements on mixtures of samples and reagents under investigation, another aim is to make fluorescence polarization measurements on the mixtures in the same analytical device.

SUMMARY OF THE INVENTION

The invention concerns an analytical system in which a large number of analytical samples can be processed with very great flexibility with regard to the analytical profile obtained from the individual sample. More particularly, the invention provides a processing station for an analytical system which is suitable for making fluorescence polarization measurements.

The aims of the invention are achieved by means of a processing station. The processing station is separated from a conveyor and contains a measuring device means for making fluorescence polarization measurements on a sample in a cell. It also contains an automatically controlled change-over and positioning means for removing individual cells from the conveyor, transferring a removed cell to a measuring position in the measuring device, and returning the cell to its original position on the conveyor after the measurement.

Preferably, the change-over and positioning device contains a pivotable hood means for screening the cell from outside light during the fluorescence polarization measurement and means for controlling the motion of the movable components of the change-over and positioning device and for pivoting the hood.

In a preferred embodiment, the change-over and positioning device contains means for optionally removing a cell from two different positions on the conveyor, for transferring a removed cell to a measuring position in the measuring device, and for returning the cell to its original position on the conveyor after the measurement.

The processing station according to the invention is preferably used in an analytical device described in detail in European Patent Application No. 92105903.9 entitled "An analytical apparatus" which corresponds to U.S. application Ser. No. 08/041,301, filed Mar. 31, 1993, now abandoned. Reference is hereby made to the description in the U.S. Ser. No. which is incorporated herein.

DESCRIPTION OF THE DRAWINGS

An embodiment of the processing station according to the invention will be described with reference to the accompanying drawings in which.

DESCRIPTION OF THE PREFERRED EMBODIMENT

Figure 1:
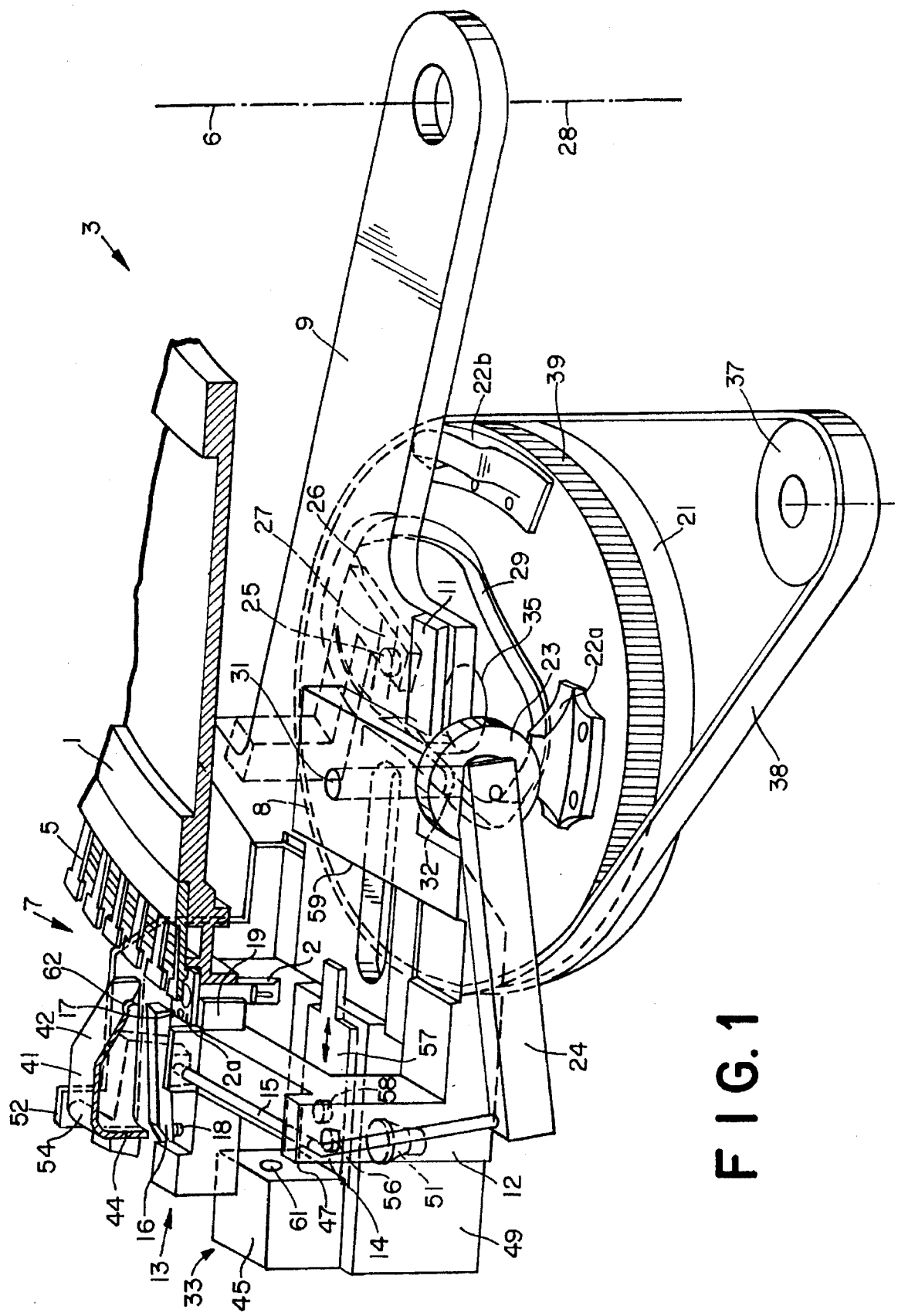
FIG. 1 shows a processing station in perspective representation at the time when a measurement cell 2 is being gripped so as to be taken from a rotor magazine 3.

The present invention concerns a processing station for making a fluorescence polarization measurements on samples in a plurality of cells under examination in a device for chemical and biochemical analysis. The analytical device contains a conveyor for conveying cells. The processing station is separated from but communicates with the conveyor. The device comprises a measuring device means for making fluorescence polarization measurements on the sample in the cell at a measuring position. It also incudes an automatically controlled change-over and positioning device for removing individual cells from the conveyor, transferring a removed cell to a measuring position in the measuring device means, and returning the cell to its original position on the conveyor after the fluorescence polarization measurement is completed.

In a preferred embodiment, the changeover and positioning device means further includes pivotable hood means for screening the cell from outside light during the fluorescence polarization measurement, and means for pivoting the hood for screening the cell from outside light.

The change-over and positioning device means preferrably includes means for removing a cell from two different positions on the conveyor, for transferring a removed cell to a measuring position in the measuring device and for returning the cell to its original position on the conveyor after the fluorescence polarization measurement.

A preferred processing station 3 according to the invention will be described. The processing station is used to make a fluorescence polarization measurement on a sample in a cell 2 under examination in a device for chemical and biochemical analysis.

The analytical device contains a circular rotor magazine 1, shown in part in FIGS. 1, 2, 7 and 8. The rotor magazine serves as a conveyor for conveying cells to various individual processing stations disposed around the circumference of the rotor magazine in the analytical device. The rotor magazine can be moved through exact angular steps in either directions of rotation by a drive mechanism (not shown in the accompanying drawings) to position A or B.

The flanges 2a (FIGS. 1 and 9) of the cells 2 are held by leaf springs 5 (FIG. 1) on the peripheral edge 4 (FIG. 2) of the rotor magazine 1 and in defined optional positions at angles of 360/n degrees, where n denotes the total number of optional positions. The rotor magazine 1 is mounted for rotation around an axis 6 and is driven (e.g., by a computer-controlled stepping motor (not shown)), so that each optional position in the rotor magazine 1 can be obtained relative to processing station 3 for making fluorescence polarization measurements.

The cells 2 are held on the outer edge of the rotor magazine. That is, they have a flange 2a on their top surface which rests on a flat annular surface at fight angles to the axis of rotation of the rotor magazine. One of the wall surfaces of the cells abuts the substantially cylindrical outer surface of the rotor magazine. The cells also are held by resilient tongues on the leaf springs 5, which project radially outwardly over the cell and are associated with each cell position. For this purpose the peripheral edges 4 are formed on their underside with a projection (not shown) which engages in a recess in the cell flange 2a. The resilient tongue holder 5 holds the cells sufficiently firmly to prevent them falling out when the magazine rotates. The resilient tongue holder also enables the cells to be easily removed or inserted manually or by a mechanical gripping mechanism.

A detailed description of the rotor magazine and operation thereof is given in European Patent Application No.92105902.8 entitled "A conveyor for an analytical apparatus", which corresponds to U.S. Ser. No. 08/040,043, filed Mar. 30, 1993, now abandoned. Reference is hereby made to the description in the U.S. Ser. No. which is incorporated herein.

The cells 2, the contents of which can be subjected to a fluorescence polarization measurement, are brought by the rotor magazine 1 into the range of action of the processing station 3. This is accomplished to grip one of the cells, to move the gripped cell into the measuring position, and to return the cell to the rotor magazine after measurement.

The processing station 3 is disposed in a predetermined, exactly deemed position relative to the rotor magazine and the cells thereon.

Figure 2:
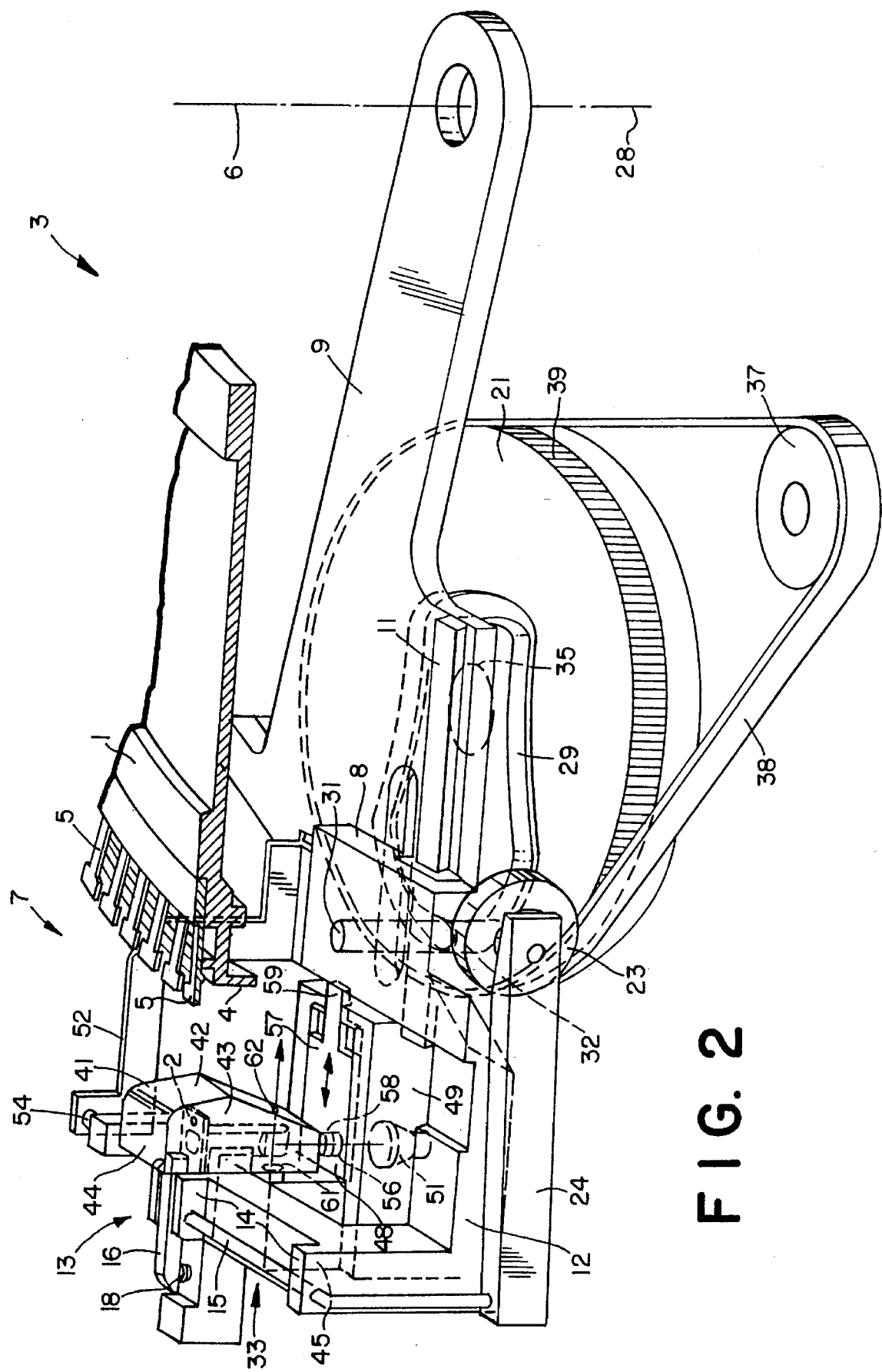
FIG. 2 shows the processing station in FIG. 1 with the cell 2 in a measuring position for a fluorescence polarization measurement by device 33.

As shown more particularly in FIGS. 1 and 2, the processing station 3 contains a device 33 for making fluorescence polarization measurements on a sample in a cell 2, and a change-over and positioning device for removing individual cells 2 from the rotor magazine 1, transferring a removed cell to a measuring position in the measuring device 33, and returning the cell to its original position on the rotor magazine after conducting the measurement.

The change-over and positioning device is constructed as follows:

A gripper 7, via a slide 8, co-operates with a guide track 11 on a swivel arm 9, so that the tongs 13 of the gripping device 7 are horizontally and longitudinally guided. This corresponds to guiding radially relative to the axis of rotation 6 of the rotor magazine 1.

The tongs 13 are disposed on a holding arm 12 projecting from the slide 8. The tongs grip in a direction along a plane which coincides with the plane in which the cells 2 are conveyed in the rotor magazine 1. The tongs 13 can therefore be moved and brought into engagement with the cells 2 radially relative to the axis 6.

A gripper control shaft 15 is mounted in bearing blocks 14 on the arm 12 and a movable gripping means in the form of a rocker 16 is non-rotatably connected to one end of shaft 15. The end of gripping means 16 near the rotor 1 has a downwardly extending (i.e., generally parallel to axis 6) lug 17 for positive engagement in a recess 2b (see FIG. 3) in a flange 2a on the cell. The end of the gripping means 16 that is remote from the rotor bears on arm 12 via a compression spring 18 so that the gripping means is rotated about shaft 15 in a direction so as to press flange 2a against a bearing table 19 integrally formed on the arm 12. The previously described device, when actuated, can reliably grip a cell 2 by flange 2a, remove it from the magazine 1, transfer it to a measuring position in the measuring plane of device 33, and return the cell to the magazine 1.

The gripping motion of the means 16 is brought about by cams 22a, and 22b disposed on the surface of a control disc 21, and is transmitted to the shaft 15 by a runner 23 and a swivel crank arm 24.

With references to FIGS. 3–6, the swivel arm 9 (via an extension arm 26 comprising a guide roller 25) is movable in a control groove 27 formed underneath the control disc 21, around an axis 28 coinciding with the axis of rotation 6 of the rotor magazine 1. When the control disc 21 suitably rotates, the arm is movable from a neutral position (FIG. 23) in one or the other direction into substantially three angular positions as follows:

1. Tongs 13 radially in line with a cell 2 which is positioned in optional position A (FIG. 4) of the rotor magazine 1.
2. Tongs 13 moved into the measuring plane of device 33 (FIG. 5) or
3. Tongs 13 radially in line with a cell 2 which is positioned in optional position B (FIG. 6) of the rotor magazine 1.

For example, the angle through which the arm 9 pivots from optional position A or B to the measuring plane can in each case be 360/n degrees. Thus, the complete angle through which the arm 9 pivots from A to B will be 2×360/n degrees.

A control groove 29 in the top surface of the control disc 21 brings about radial motion of the tongs 13 in the direction of the axis of process station 3 so as to i) grip a cell 2 from the optional position A or B, or ii) radially return it, or iii) remove a cell 2 from the rotor magazine 1 and transfer it to a measuring position in the measuring device 33, or iv) move tongs 13 in the opposite direction when returning the cell 2 to the rotor magazine 1. The slide 8 of the gripping device 7 is operatively connected to the control groove 29 via a pin 31 and a guide roller 32. The gripping device 7, considered radially relative to the rotor axis 6, can move from a neutral position (FIG. 3) into two other positions, irrespective of the direction of motion of the control disc 21, as follows:

1. A position near the rotor (FIGS. 4, 6 and 7) for gripping or transferring a cell 2 from the rotor magazine 1 and
2. A position remote from the rotor (FIGS. 5 and 8), which is the measuring position.

Figure 7:
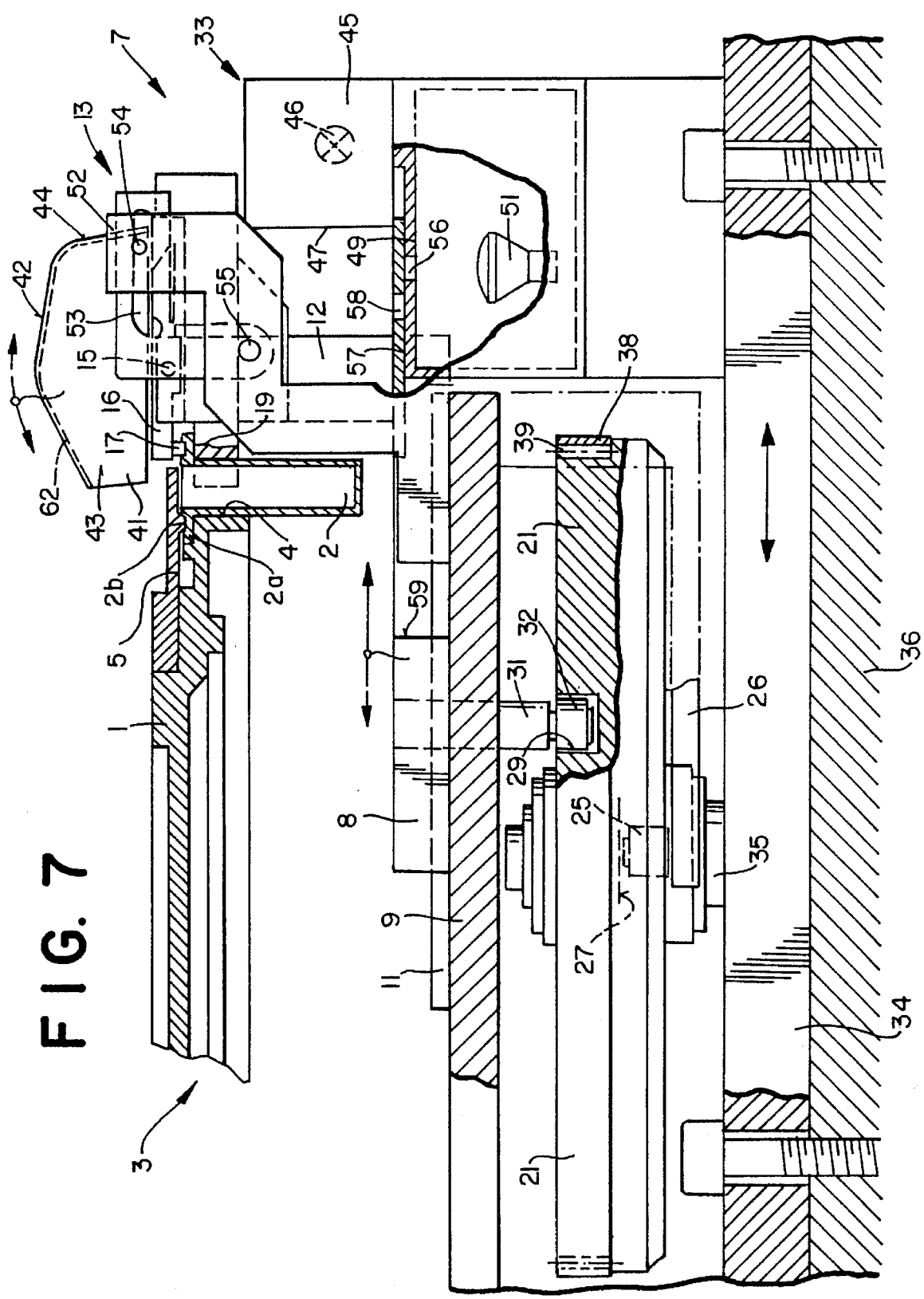
FIG. 7 is a side view of the processing station, partly in section, having a cut out area corresponding to arrow VII in FIG. 4.
Figure 8:
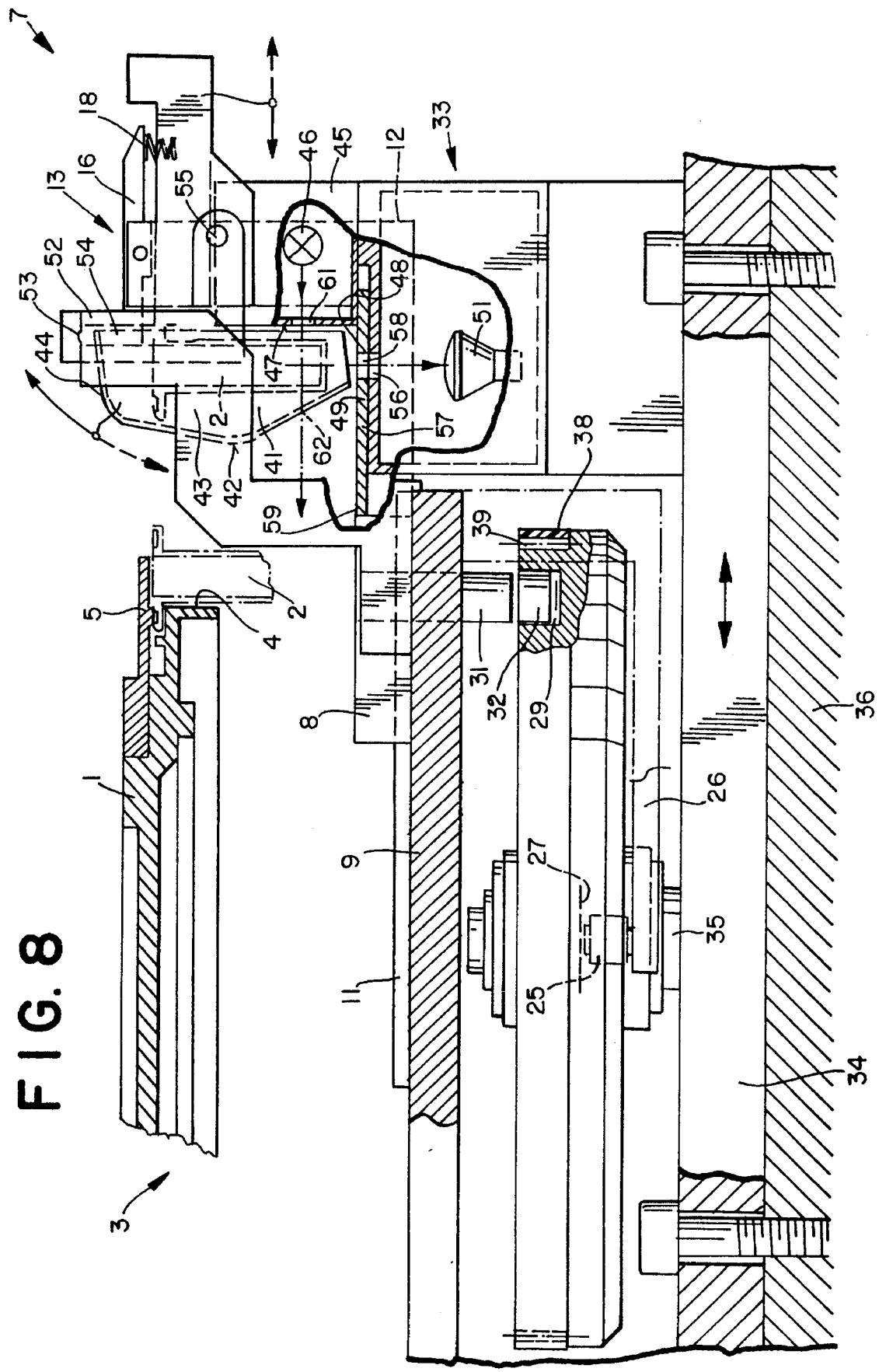
FIG. 8 is a side view, partly in section, of the processing station, having a cut out area corresponding to arrow VIII in FIG. 5.

With reference to FIGS. 7 and 8, the control disc 21 is rotatably mounted on a shaft secured to a baseplate 34, so that the extension arm 26 of the swivel aim 9 is disposed between the baseplate 34 and the control disc 21, and the guide roller 25 can engage in the control groove 27. The baseplate 34 is adjustably secured to the base 36 of the casing, for accurately positioning the gripping device 7 relative to the rotor magazine 1 (FIGS. 7 and 8). The motor (not shown), via a toothed wheel 37 (FIG. 1) and a toothed belt 38 (FIGS. 1, 7 & 8), chives the control disc 21, which has corresponding teeth 39 on its outer periphery (FIGS. 1 and 2). The rotation of the control disc is controlled and monitored by computer (not shown) in accordance with conventional techniques.

The previously-described components of the change-over and positioning device function and co-operate as follows.

Since the control grooves 27, 29 are formed on a common control disc 21 and are thus driven in synchronism by a computer-controller stepping motor (not shown), the pivoting motion (rotational with respect to axis 6) of the arm 9 overlaps the linear motion (radially in or outwardly) of the gripping device 7, such motion being radial relative to the axis 6, so that the total motion is as follows.

Figure 3:
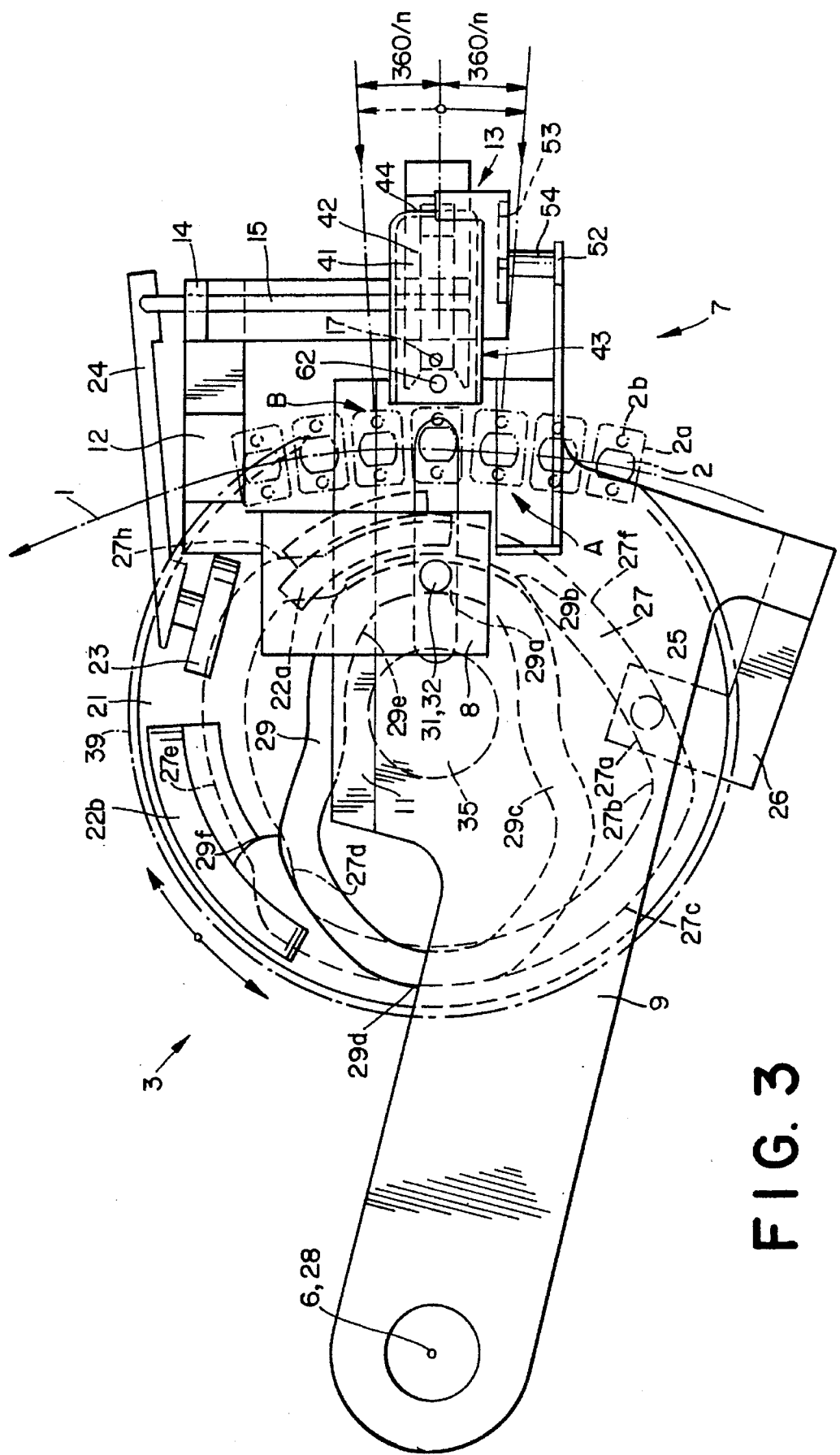
FIG. 3 is a plan view of the processing station of FIG. 1, in a neutral or starting position.

When the gripping device 7 is in a neutral position as per FIG. 3, the guide rollers 25, 32 of the swivel arm 9 and the gripping device 7 engage corresponding portions 27a, 29a of the cams on the control discs 27, 29, respectively.

As soon as the rotor magazine 1 has stopped in a predetermined, suitable position, a cell 2 can be taken from the optional position A or B by suitably rotating the control disc 21 to a predetermined position.

Figure 4:
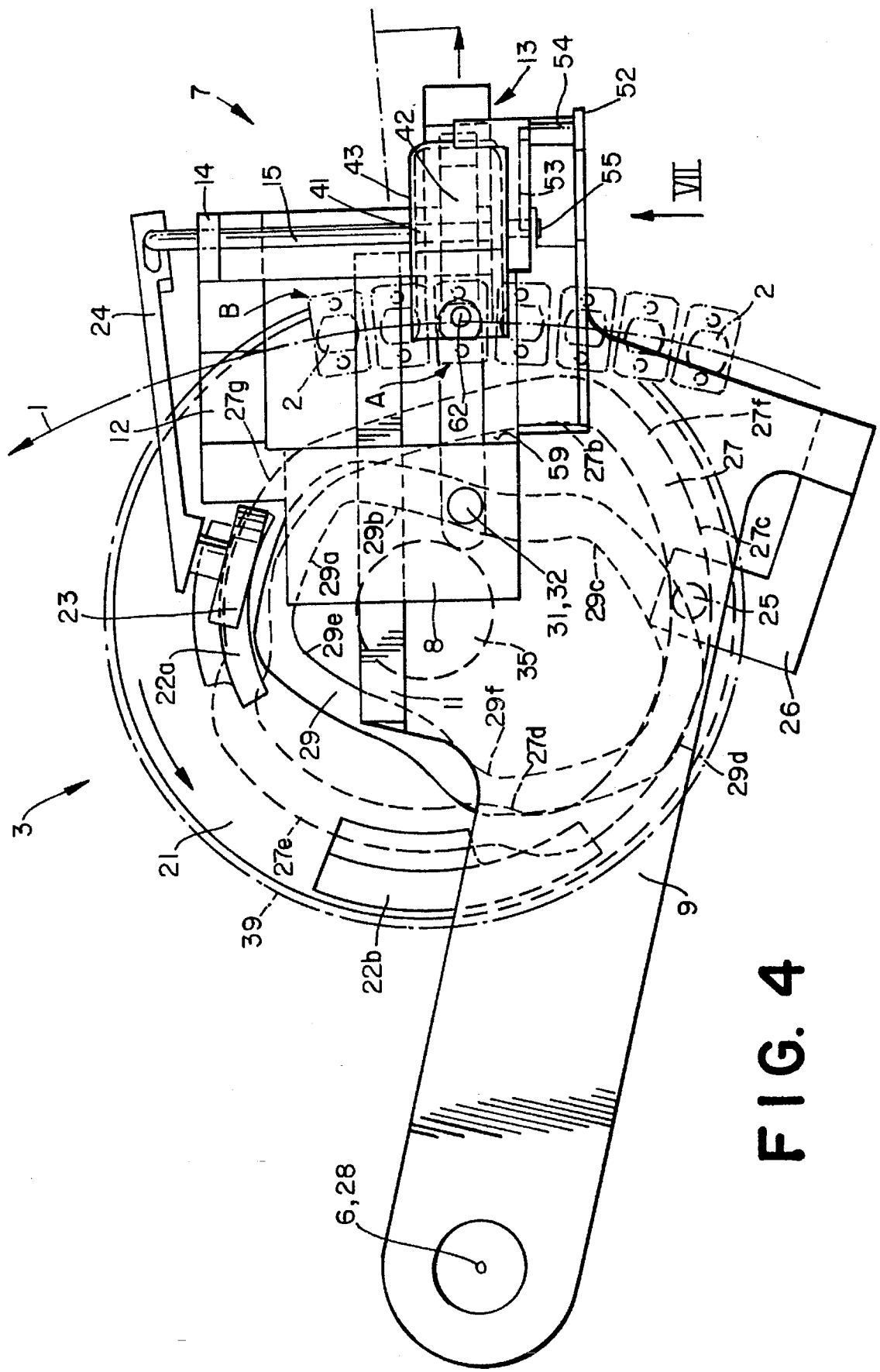
FIG. 4 is a plan view of the processing station in FIG. 1 in a gripping position relative to selection of a cell 2, which cell is in position A on the rotor magazine 3.

When the control disc 21 rotates counter-clockwise (with respect to the plan view shown in FIG. 3), the arm 9, controlled by portion 27b of the control groove 27, first pivots 360/n degrees (n=number of positions) clockwise and remains there (portion 27c of cam 27) in front of the optional position A of magazine 1 or in front of the cell 2. The gripping device 7 is then moved towards the rotor 1 by the portion 29a of the cam 29, via the slide 8 or guide roller 32. Meanwhile, the roller 23 of the tongs-opening mechanism 15, 24 runs against a control cam 22a permanently disposed on disc 21 and opens the tongs 13. If the tongs 13 are in the gripping position, the cam 22a or the compression spring 18 closes the tongs 123. Portion 29c of cam 29 now moves the tongs 13 back or removes the cell 2 from the rotor 1 (FIG. 4). When cell 2 has been removed from rotor 1, the guide roller 25 of the swivel arm 9 reaches portion 27d of cam 27 and pivots arm 9 through 360/n degrees counterclockwise and remains there (portion 27e of 27).

As soon as the tongs 13 have reached an end position remote from the rotor (the control roller 32 is in portion 29d of cam 29), the isolated cell 2 is positioned in the measuring position in the measuring device 33. The control disc drive is then stopped and the measurement can be made.

After the measurement, the control disc 21 is driven clockwise, so that the cell 2, after the measurement, is returned in the opposite direction to the rotor magazine 1 or optional position A.

The gripping device 7 then returns to a neutral position and the control disc drive is stopped. While a cell 2 is being brought into the measuring station 33, the rotor magazine can of course continue to rotate and carry out other operations, but when the cell 2 has been returned to the rotor 1, the previous position must be restored.

If the gripper 7 is to remove a cell 2 from the optional position B, the control disc 21 is moved from the neutral position in the clockwise direction (with respect to the plan view shown in FIG. 3). The control roller 25 on the swivel arm 9 now runs in a portion 27f of cam 27 and pivots arm 9 through 360/n degrees counter-clockwise and remains in radial alignment with the optional position B (portion 27g of 27). The tongs 13 are radially moved in the direction of the rotor axis 6 by a portion 29e of cam 29. An additional cam 22b on the control disc controls the movement of tongs 13. The cell 2 is transferred to and from the measuring position 33 as described in the case of the optional position A. Arm 9 is pivoted into the measuring plane via portion 27h of control groove 27 and linear motion into the measuring position is brought about via portion 29f of the control groove 29.

When the previously-described preferred embodiment of the processing station 3 is used, an empty cell (for use as a blank or normalization measurement) is taken from optional position A whereas a cell containing a sample for investigation is taken from the optional position B. This saves time during measurement.

In a variant of the previously-described embodiment, processing station 3 contains a simplified version of the change-over and positioning device. In this embodiment, the cell 2 is always taken from the same position on the rotor magazine 1. This variant is of use in analytical devices in which the time sequences obviate the need for a facility for taking cells for idle measurements from a different optional position from cells containing samples to be measured.

Measuring device 33 for making fluorescence and polarization measurements and diagrammatically shown in FIGS. 1 and 2 will be described in detail with reference to FIGS. 7, 8 and 9.

Figure 9:
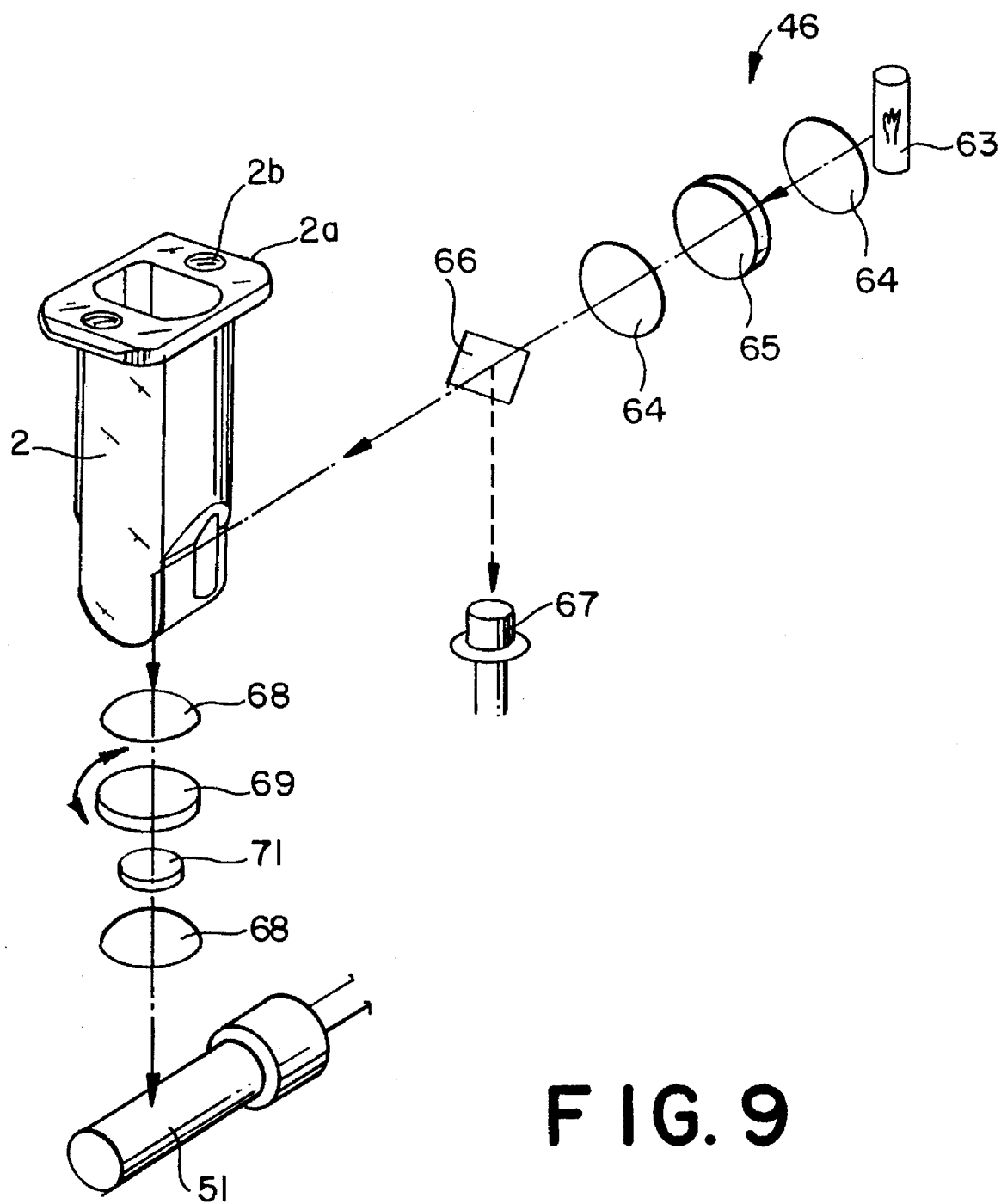
FIG. 9 diagrammatically shows the construction of a measuring device for making a fluorescence polarization measurement on a sample in a cell.

FIG. 9 diagrammatically shows the optical arrangement of the measuring device 33. The device comprises a measuring-light source 46, including a halogen lamp 63, a lens system 64 and an interference filter 65 for the preselected excitation wavelength. In order to monitor the light intensity or to compensate for fluctuations in intensity by computer, a beam splitter 66 is disposed in the path of the measuring light source 46. The beam splitter 66 conveys a part of the measuring-light beam to a photodiode 67 which delivers signals for additional processing. The remainder of the measuring-light beam travels through cell 2 and excites its sample contents. The light emitted by the sample contained in cell 2 during a fluorescence-polarization measurement is supplied via a lens system 68 and an interference filter 71 to a photomultiplier 51 which delivers a corresponding measurement signal. A polarizer 69 disposed in the path of the light emitted by the sample and drivable by a motor (not shown) can make two different measurements. These occur at polarization angles of 0° or 90°.

As shown in FIGS. 1, 2, 7 and 8, the measuring-light source 46 is disposed in a casing 45, and the photomultiplier 51 is disposed in a casing 49. As shown in FIGS. 7 and 8, the measuring duct or entry opening 56 of the photomultiplier 51 is closable by a slide 57. When, and only when, the cell 2 is in the measuring position, an opening 58 through the slide is in line with an entry opening 56 in the photomultiplier casing 49. The slide 57 is actuated via an abutment surface 59 on carriage 8 of the gripper device 7, which can act directly on slide 57. The closing motion can be brought about, for example, by leaf springs (not shown). When the slide 57 is closed, the photomultiplier current can be measured in darkness.

During the measurement, the measuring light is supplied horizontally, in the direction towards the rotor-magazine axis 6, through an outlet opening 61 (FIG. 8) to a measuring cell 2. The light travels through and excites the contents of the cell and can leave the measuring chamber through a small opening 62 in the front wall 42 of the hood 41, to avoid interfering reflections.

The light emission, which gives information about the contents of the cell, is measured by a photomultiplier 51 disposed vertically under the cell.

A more preferred embodiment of the processing station 3 contains a hood 41, (FIG. 7) which is mounted for pivoting through 90° on the holding or gripper arm 12 and has a front wall 42, two side walls 43 and a top wall 44.

As shown in FIGS. 1, 3 4, 6 and 7, when the tongs 13 hold the cell 2 in positions outside the measuring position in the measuring device 33, the hood 41 is substantial horizontal. However, the cell 2 is exposed and the hood 41 does not interfere with the required transfer processes.

Figure 5:
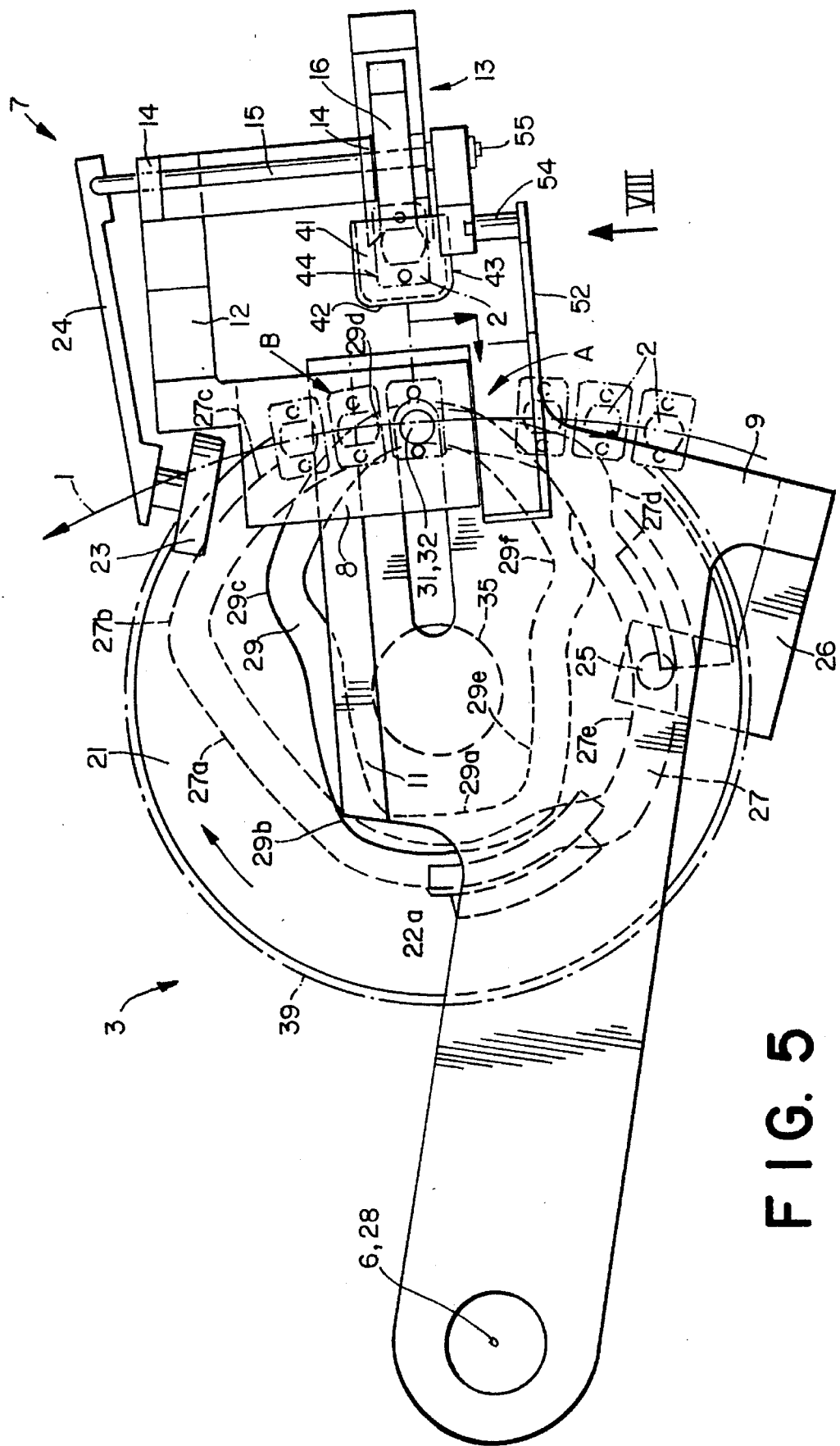
FIG. 5 is a plan view of the processing station in FIG. 2, in which a cell 2 is brought into the measuring position in the measuring device 33.
Figure 6:
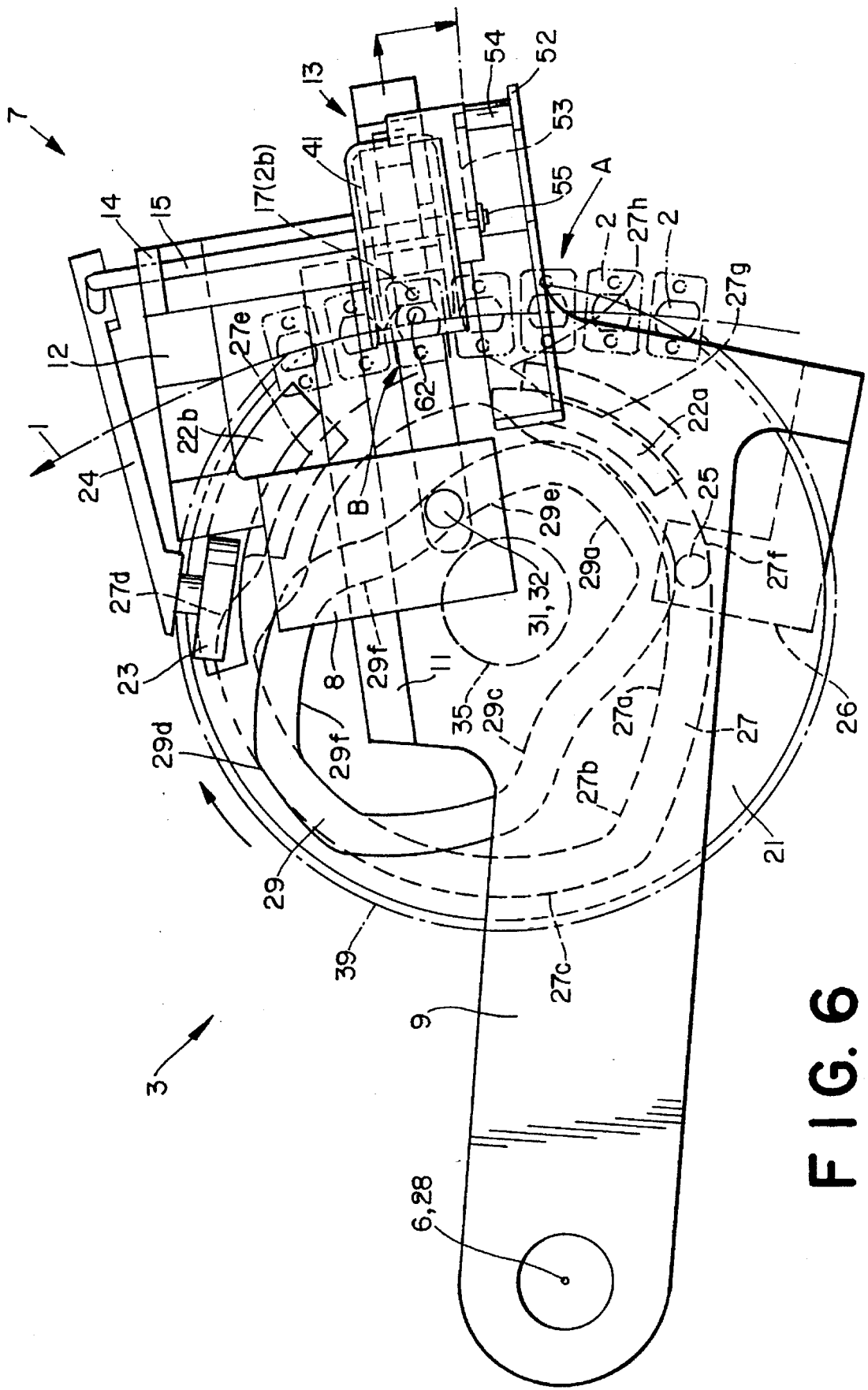
FIG. 6 is a plan view of the processing station in FIG. 1 in a gripping position relative to selection of a cell 2, which cell is in position B on the rotor magazine 3.

As shown in FIGS. 2, 5 and 8, when the tongs 13 hold the cell in the measuring position in the measuring device 253, the hood 41 is pivoted through 90° to the vertical and surrounds the cell on four sides. It cooperates with the wall of the casings 45 and 49 to form a dark chamber which screens the cell from outside light.

in order to control the motion of the hood 41, an extension arm 52 is secured to the swivel arm 9 and ends in a control pin 54 which engages in a control groove 53 in hood 41. Pin 54 is at a vertical distance from the axis 55 of hood 41 (FIGS. 7, 8). The motion of pin 54 relative to axis 55, (i.e., when the carriage 8 moves along the side 11 on arm 9 during the motion of the gripping device 7 towards the measuring position) results in a corresponding rotation (see FIGS. 7 and 8) of hood 41, bringing it to the position shown in FIGS. 2, 5 and 8.

As can be seen from the previously-described means for controlling the motion of the hood 41, the motion is controlled by the same previously-described means which control the motion of the change-over and positioning device.

In a fluorescence polarization measurement, the cell 2 being measured has to be screened from outside light. This is because the measurement must be made in a dark chamber. In the measuring position 33, the cell 2 is kept dark by hood 41 mounted on gripper arm 12 so as to be pivotable through 90°. The hood substantially surrounds cell 2, during measurement in the measuring device 33, on four sides. This is a front wall 42, two side walls 43 and a top wall 44.

In measuring position for device 33, the tongs 13, the cell 2 and the hood 41 are moved up to the casing 45 of the measuring-light source, so that the casing substantially constitutes the back wall 47 of the dark chamber. The floor 48 (FIG. 8) of the dark chamber is formed by a part 49 of the photomultiplier casing so as to form a measuring channel.

In every position of the tongs 13 outside the measuring position of device 33, the hood 41 is pivoted through 90°. As a result, the cell 2 is exposed so as to not interfere with the required conveying processes.

The invention has been described with reference to specifically preferred embodiments. Additional embodiments within the skill of an artisan and the spirit of the invention are contemplated and intended to be included within the inventive concept.

I claim:

1. A processing station for making fluorescence polarization measurements on samples in a plurality of cells under examination in an analytical apparatus, the analytical apparatus containing a conveyor for conveying cells, the processing station being separated from the conveyor, the processing station comprising:

(a) measuring means for making fluorescence polarization measurements on the sample in the cell at a measuring position; and (b) automatically controlled change-over and positioning means comprising (1) means for removing an individual cell from a position on the conveyor, (2) means for transferring the removed cell to the measuring position in the measuring means, and (3) means for returning the cell to a position on the conveyor after the fluorescence polarization measurement is completed, the change-over and positioning means further comprising (4) pivotable hood means for screening the cell from outside light during the fluorescence polarization measurement, and (5) means for pivoting the pivotable hood means for screening the cell from outside light, the means for pivoting the pivotable hood means and the means for transferring the cell to the measuring position including a cam and cam follower drive means and respective mechanical control linkage means to connect the drive means with the means for transferring the cell to the measuring position and to coordinate operations of removing means, transferring means, returning means and pivoting means.

2. The processing station of claim 1, wherein the change-over and positioning means further comprises means for removing a cell from two predetermined positions on the conveyor, means for transferring a removed cell to a measuring position in the measuring means, and means for returning the cell to its original position on the conveyor after the fluorescence polarization measurement is completed.

* * * * *

UNITED STATES PATENT AND TRADEMARK OFFICE
CERTIFICATE OF CORRECTION

PATENT NO. : 5,496,519
DATED : March 5, 1996
INVENTOR(S) : Gottlieb Schacher

It is certified that error appears in the above-indentified patent and that said Letters Patent is hereby corrected as shown below:

On the title page of the patent, please delete "[*] Notice: The portion of the term of this patent subsequent to Jan. 24, 2012, has been disclaimed." and insert -- [*] Notice: The portion of the term of this patent subsequent to April 19, 2013, has been disclaimed. --

Signed and Sealed this

Fourth Day of June, 1996

Attest:

BRUCE LEHMAN

*Attesting Officer*     *Commissioner of Patents and Trademarks*